US012649708B2

(12) United States Patent
Arai et al.

(10) Patent No.: US 12,649,708 B2
(45) Date of Patent: Jun. 9, 2026

(54) α,β-UNSATURATED ALDEHYDE PRODUCTION METHOD

(71) Applicant: Kao Corporation, Tokyo (JP)

(72) Inventors: Tsubasa Arai, Wakayama (JP); Kensuke Masumura, Tokyo (JP)

(73) Assignee: Kao Corporation, Tokyo (JP)

( * ) Notice: Subject to any disclaimer, the term of this patent is extended or adjusted under 35 U.S.C. 154(b) by 630 days.

(21) Appl. No.: 18/005,716

(22) PCT Filed: Jul. 8, 2021

(86) PCT No.: PCT/JP2021/025805

§ 371 (c)(1),
(2) Date: Jan. 17, 2023

(87) PCT Pub. No.: WO2022/019141

PCT Pub. Date: Jan. 27, 2022

(65) Prior Publication Data

US 2023/0278946 A1 Sep. 7, 2023

(30) Foreign Application Priority Data

Jul. 20, 2020 (JP) ................................ 2020-123978

(51) Int. Cl.
*C07C 45/72* (2006.01)
*C07C 45/74* (2006.01)

(52) U.S. Cl.
CPC .......... *C07C 45/74* (2013.01); *C07B 2200/13* (2013.01)

(58) Field of Classification Search
CPC ...................................................... C07C 45/72
See application file for complete search history.

(56) References Cited

U.S. PATENT DOCUMENTS 5,081,311 A 1/1992 Huellmann et al.
5,728,892 A * 3/1998 Kuiterman .............. C07C 45/74 568/433
10,981,853 B2 * 4/2021 Arai ...................... C07C 47/232
2003/0009058 A1 1/2003 Canos et al.
2009/0171124 A1 7/2009 Ishida et al.
2010/0137620 A1 6/2010 Andrey
2011/0021845 A1 1/2011 Zim et al.
2012/0004468 A1 1/2012 Tate et al.
2012/0004469 A1 1/2012 Martenak et al.
2020/0347003 A1 11/2020 Arai et al.

FOREIGN PATENT DOCUMENTS

EP 0 095 783 A2 12/1983
JP 58-219139 A 12/1983
JP 62-221451 A 9/1987
JP 63-225329 A 9/1988
JP 3-81242 A 4/1991
JP 3-220152 A 9/1991
JP 10-59892 A 3/1998
JP 2003-512345 A 4/2003
JP 2007-153764 A 6/2007
JP 2007-153818 A 6/2007
JP 2010-527991 A 8/2010
JP 2011-517656 A 6/2011
JP 2012-11378 A 1/2012
JP 2012-11379 A 1/2012
JP 2015-44775 A 3/2015

(Continued)

OTHER PUBLICATIONS

International Search Report issued Aug. 24, 2021 in PCT/JP2021/025805 filed on Jul. 8, 2021, 3 pages.

El Kadib et al., "Improving Catalytic Activity by Synergic Effect between Base and Acid Pairs in Hierarchically Porous Chitosan@Titania Nanoreactors", Organic Letters, 2010, vol. 12, No. 5, p. 948-951, Supporting informations, Abstract, Table 3, Supporting informations (1.4. Preparation of titanium dioxide microspheres).

(Continued)

*Primary Examiner* — Sikarl A Witherspoon

(74) *Attorney, Agent, or Firm* — Oblon, McClelland, Maier & Neustadt, L.L.P.

(57) ABSTRACT

A method for producing an α,β-unsaturated aldehyde, including reacting a compound represented by formula (I) with a compound represented by formula (II) in the presence or absence of a solvent to provide a compound represented by formula (III), wherein titanium oxide is used as a catalyst, and an amount of the solvent is 50 parts by mass or less relative to 100 parts by mass in total of the compound of formula (I) and the compound of formula (II), (I)

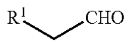

(II)

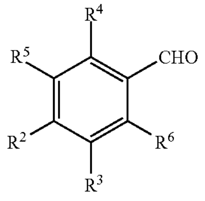

(III)

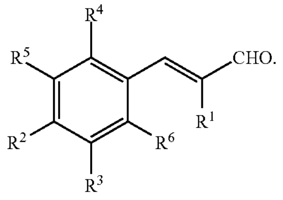

18 Claims, No Drawings

(56) References Cited

FOREIGN PATENT DOCUMENTS

| | | | |
|---|---|---|---|
| JP | 2019-104718 | A | 6/2019 |
| WO | WO 2019/116608 | A1 | 6/2019 |

OTHER PUBLICATIONS

Vrbkova et al., "Aldol condensation of benzaldhyde and heptanal: a comparative study of laboratory and industrially prepared Mg—Al mixed oxides", Journal of Chemical Technology and Biotechnology, 2018, vol. 93, No. 1, p. 166-173 Abstract, Table 3, p. 170, left column, first paragraph.

Zhao et al., "$TiO_2$-Catalyzed n-Valeraldehyde Self-Condensation to 2-Propyl-2-Heptenal: Acid Catalysis or Base Catalysis?", Industrial & Engineering Chemistry Research, 2016, vol. 55, No. 48, p. 12326-12333 Abstract, 2.4 Catalysts activity.

Extended European Search Report issued Sep. 10, 2024 in European Patent Application No. 21846154.9, 6 pages.

Office Action mailed on Dec. 24, 2025, in corresponding India Patent Application No. 202317008141(with English translation).

Dong Nguyen Thanh et al., Nanosized TiO2—A promising catalyst for for the aldol condensation of furfural with acetone in biomass upgrading, Catalysis Today, vol. 277, Part 1, 201, pp. 97-107, ISSN 09205861, https://doi.org/10.1016/j.cattod.2015.11.027. Published Nov. 15, 2016.

* cited by examiner

α,β-UNSATURATED ALDEHYDE PRODUCTION METHOD

CROSS REFERENCE TO RELATED APPLICATIONS

This application is a National Stage entry under 35 U.S.C. § 371 of PCT/JP2021/025805, filed on Jul. 8, 2021, and claims priority to Japanese Patent Application No. 2020-123978, filed on Jul. 20, 2020. The entire contents of both are incorporated herein by reference.

TECHNICAL FIELD

The present invention relates to a method for producing an α,β-unsaturated aldehyde.

BACKGROUND ART

An aldehyde is a useful compound as, e.g., a material for a chemical reaction, or an intermediate for perfume, medicine, or agricultural chemicals. In particular, an α,β-unsaturated aldehyde having a specific molecular weight is useful in itself as a fragrance material, and further is also used as a raw material for derivatives with different fragrance notes.

As a method for producing an aldehyde, for example, dehydrogenation or oxidation using alcohol as a raw material has conventionally been known. In particular, a cross-aldol condensation reaction between two types of aldehydes is frequently used as a method for producing an α,β-unsaturated aldehyde, and various studies have been made on the reaction conditions of the cross-aldol condensation reaction.

For example, Org. Lett. 2010, 12(5), 948 (Non-Patent Document 1) discloses a method for producing an α,β-unsaturated aldehyde by the cross-aldol reaction of heptanal and benzaldehyde. In this reaction, titanium oxide is used as a catalyst, and in a case of using a solvent, a large amount of the solvent is used.

JP 2019-104718 A (Patent Document 1) discloses a method for adjusting the water content in materials used for reaction to a specific amount in the cross-aldol condensation reaction.

DISCLOSURE OF INVENTION

The present invention provides a method for producing an α,β-unsaturated aldehyde, including a step of reacting a compound represented by formula (I) (hereinafter, also referred to as a "compound of formula (I)") with a compound represented by formula (II) (hereinafter, also referred to as a "compound of formula (II)") in the presence or absence of a solvent to provide a compound represented by formula am (α,β-unsaturated aldehyde), wherein titanium oxide is used as a catalyst in the step, and an amount of the solvent is 50 parts by mass or less relative to 100 parts by mass in total of the compound of formula (I) and the compound of formula (II).

[Chemical Formula 1]

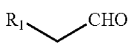

(I)

-continued (II)

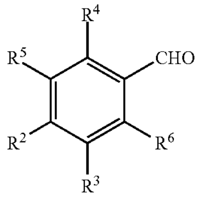

(III)

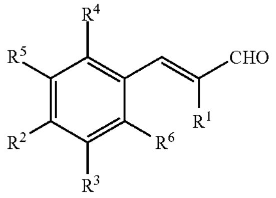

In the above formulae, $R^1$ represents a hydrogen atom or an alkyl group having 1 or more and 10 or less of carbon atoms, $R^2$ represents a hydrogen atom, an alkyl group having 1 or more and 6 or less of carbon atoms, or an alkoxy group having 1 or more and 6 or less of carbon atoms, and $R^3$ represents a hydrogen atom or an alkyl group having 1 or more and 3 or less of carbon atoms, or $R^2$ and $R^3$ form 1,3-dioxolane together with carbon atoms to which $R^2$ and $R^3$ are attached, and $R^4$, $R^5$, and $R^6$ each independently represent a hydrogen atom or an alkyl group having 1 or more and 3 or less of carbon atoms.

DETAILED DESCRIPTION OF THE INVENTION

The cross-aldol condensation reaction is known to cause side reactions such as dimerization (self-aldol condensation reaction) and disproportionation (Cannizzaro reaction) between the same type of aldehydes. If the side reactions proceed, there are problems that it is difficult to isolate the target aldehyde, and the yield is reduced.

It is an object of the present invention to provide a method for producing an α,β-unsaturated aldehyde that enables production of a target aldehyde at a high yield with satisfactory selectivity while reducing the formation of by-products.

The present inventors found that the use of a specific catalyst in the cross-aldol condensation reaction can produce a target aldehyde at a high yield with satisfactory selectivity while reducing the formation of by-products.

Specifically, the present invention provides a method for producing an α,β-unsaturated aldehyde, including a step of reacting a compound represented by formula (I) (hereinafter, also referred to as a "compound of formula (I)") with a compound represented by formula (II) (hereinafter, also referred to as a "compound of formula (II)") in the presence or absence of a solvent to provide a compound represented by formula (III) (α,β-unsaturated aldehyde), wherein titanium oxide is used as a catalyst in the step, and an amount of the solvent is 60 parts by mass or less relative to 100 parts by mass in total of the compound of formula (I) and the compound of formula (II).

[Chemical Formula 2]

(I)

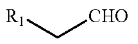

(II)

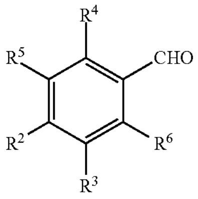

(III)

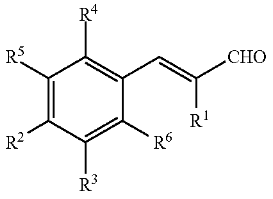

In the above formulae, $R^1$ represents a hydrogen atom or an alkyl group having 1 or more and 10 or less of carbon atoms, $R^2$ represents a hydrogen atom, an alkyl group having 1 or more and 6 or less of carbon atoms, or an alkoxy group having 1 or more and 6 or less of carbon atoms, and $R^3$ represents a hydrogen atom or an alkyl group having 1 or more and 3 or less of carbon atoms, or $R^2$ and $R^3$ form 1,3-dioxolane together with carbon atoms to which $R^2$ and $R^3$ are attached, and $R^4$, $R^5$, and $R^6$ each independently represent a hydrogen atom or an alkyl group having 1 or more and 3 or less of carbon atoms.

The present invention provides a method for producing an α,β-unsaturated aldehyde that enables production of a target aldehyde at a high yield with satisfactory selectivity while reducing the formation of by-products.

The method for producing an α,β-unsaturated aldehyde of the present invention involves the use of titanium oxide as a catalyst in the cross-aldol condensation reaction between the compound of formula (I) and the compound of formula (II). In the present invention, the term "selectivity" refers to the selectivity of the α,β-unsaturated aldehyde (relative to the compound of formula (II)) determined by the method described in Examples, the term "yield" refers to the yield of the α,β-unsaturated aldehyde (relative to the compound of formula (I)) determined by the method described in Examples, and the reducing the formation of by-products means a high HCA-to-dimer formation ratio described in Examples.

Compound Represented by Formula (I)

In the compound represented by formula (I), $R^1$ represents a hydrogen atom or an alkyl group having 1 or more and 10 or less of carbon atoms. $R^1$ is preferably an alkyl group having 1 or more and 10 or less of carbon atoms, and more preferably an alkyl group having 3 or more and 8 or less of carbon atoms. From the viewpoints of the reactivity of the cross-aldol condensation reaction and the usefulness of the resultant aldehyde as a fragrance material, the alkyl group having 1 or more and 10 or less of carbon atoms is preferably an alkyl group having 2 or more carbon atoms, and more preferably an alkyl group having 3 or more carbon atoms. Furthermore, the alkyl group having 1 or more and 10 or less of carbon atoms is preferably an alkyl group having 8 or less carbon atoms, and more preferably an alkyl group having 7 or less carbon atoms. The alkyl group having 1 or more and 10 or less of carbon atoms may be either a straight-chain alkyl group or a branched-chain alkyl group, and is preferably a straight-chain alkyl group. Examples of the alkyl group having 1 or more and 10 or less of carbon atoms include methyl, ethyl, n-propyl, isopropyl, 2-methylpropyl, n-butyl, t-butyl, pentyl, hexyl, heptyl, octyl, nonyl, and decyl. Examples of the compound of formula (I) include acetaldehyde, propionaldehyde, butanal, pentanal, hexanal, heptanal, octanal, nonanal, decanal, and dodecanal. From the viewpoint of the reactivity of the cross-aldol condensation reaction, the compound of formula (I) is preferably propionaldehyde, butanal, pentanal, hexanal, heptanal, octanal, nonanal, or decanal, more preferably pentanal, hexanal, heptanal, octanal, nonanal, or decanal, and further preferably pentanal, hexanal, heptanal, octanal, or nonanal.

Compound Represented by Formula (II)

In the compound represented by formula (II), $R^2$ represents a hydrogen atom, an alkyl group having 1 to 6 carbon atoms, or an alkoxy group having 1 or more and 6 or less of carbon atoms, and $R^3$ represents a hydrogen atom or an alkyl group having 1 or more and 3 or less of carbon atoms. $R^2$ is preferably a hydrogen atom or an alkyl group having 1 or more and 6 or less of carbon atoms, and more preferably a hydrogen atom. From the viewpoints of the reactivity of the cross-aldol condensation reaction and the usefulness of the resultant aldehyde as a fragrance material, the alkyl group having 1 or more and 6 or less of carbon atoms is preferably an alkyl group having 1 or more carbon atoms. Furthermore, the alkyl group having 1 or more and 6 or less of carbon atoms is preferably an alkyl group having 5 or less carbon atoms, and more preferably an alkyl group having 4 or less carbon atoms. Examples of the alkyl group having 1 or more and 6 or less of carbon atoms include methyl, ethyl, n-propyl, isopropyl, 2-methylpropyl, n-butyl, t-butyl, pentyl, and hexyl. The alkoxy group having 1 or more and 6 or less of carbon atoms is an alkyloxy group having 1 or more and 6 or less of carbon atoms. Examples of the alkoxy group having 1 or more and 6 or less of carbon atoms include methoxy, ethoxy, n-propyloxy, isopropyloxy, 2-methylpropyloxy, n-butyloxy, t-butyloxy, pentyloxy, and hexyloxy. From the viewpoints of the reactivity of the cross-aldol condensation reaction and the usefulness of the resultant aldehyde as a fragrance material, the alkoxy group having 1 or more and 6 or less of carbon atoms is preferably an alkoxy group having 1 or more and 5 or less of carbon atoms, and more preferably an alkoxy group having 1 or more and 4 or less of carbon atoms. $R^3$ is a hydrogen atom or an alkyl group having 1 or more and 3 or less of carbon atoms as described above, and preferably a hydrogen atom. From the viewpoint of the usefulness of the resultant aldehyde as a fragrance material, the alkyl group having 1 or more and 3 or less of carbon atoms is preferably an alkyl group having 1 or more and 2 or less of carbon atoms, and more preferably an alkyl group having 1 carbon atom. Examples of the alkyl group having 1 or more and 3 or less of carbon atoms include methyl, ethyl, n-propyl, and isopropyl.

In the compound represented by formula (II), $R^2$ and $R^3$ may form 1,3-dioxolane together with carbon atoms to which $R^2$ and $R^3$ are attached. In this case, the compound of formula (II) is represented by the following formula.

[Chemical Formula 3]

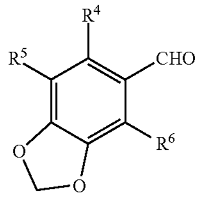

In the above formula, $R^4$, $R^6$, and $R^6$ are as defined above in the formula (II).

In the compound of formula (II), $R^4$, $R^6$, and $R^6$ each independently represent a hydrogen atom or an alkyl group having 1 or more and 3 or less of carbon atoms. $R^4$, $R^5$, and $R^6$ are preferably hydrogen atoms. From the viewpoint of the usefulness of the resultant aldehyde as a fragrance material, the alkyl group having 1 or more and 3 or less of carbon atoms is preferably an alkyl group having 1 or more and 2 or less of carbon atoms, and more preferably an alkyl group having 1 carbon atom. Examples of the alkyl group having 1 or more and 3 or less of carbon atoms include methyl, ethyl, n-propyl, and isopropyl.

The compound of formula (II) is preferably, e.g., any of the following compounds, and preferably benzaldehyde.

[Chemical Formula 4]

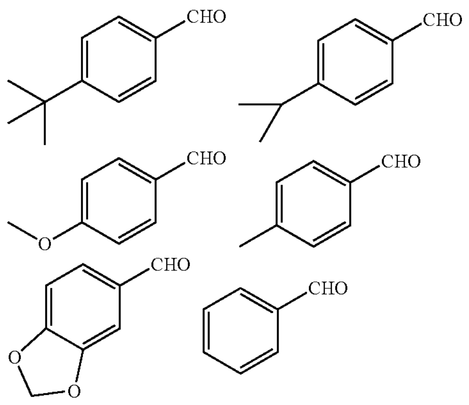

Compound Represented by Formula (III)

In the compound represented by formula (III), $R^1$ represents a hydrogen atom or an alkyl group having 1 or more and 10 or less of carbon atoms, $R^2$ represents a hydrogen atom, an alkyl group having 1 or more and 6 or less of carbon atoms, or an alkoxy group having 1 or more and 6 or less of carbon atoms, and $R^3$ represents a hydrogen atom or an alkyl group having 1 or more and 3 or less of carbon atoms, or $R^2$ and $R^3$ form 1,3-dioxolane together with carbon atoms to which $R^2$ and $R^3$ are attached, and $R^4$, $R^5$, and $R^6$ each independently represent a hydrogen atom or an alkyl group having 1 or more and 3 or less of carbon atoms.

In the compound represented by formula (III), $R^1$ is preferably an alkyl group having 1 or more and 10 or less of carbon atoms, and more preferably an alkyl group having 3 or more and 8 or less of carbon atoms, $R^2$ is preferably a hydrogen atom or an alkyl group having 1 or more and 6 or less of carbon atoms, and more preferably a hydrogen atom, and $R^3$ is preferably a hydrogen atom, and $R^4$, $R^5$, and $R^6$ are preferably hydrogen atoms.

The compound represented by formula (III) is preferably, e.g., a compound of any of the following combinations of $R^1$ to $R^6$ in Table 1.

TABLE 1

| | Combination 1 | Combination 2 | Combination 3 | Combination 4 |
|---|---|---|---|---|
| $R^1$ | Alkyl group having 1 or more and 10 or less of carbon atoms | Alkyl group having 1 or more and 10 or less of carbon atoms | Alkyl group having 3 or more and 8 or less of carbon atoms | Alkyl group having 3 or more and 8 or less of carbon atoms |
| $R^2$ | Hydrogen atom | Alkyl group having 1 or more and 6 or less of carbon atoms | Hydrogen atom | Alkyl group having 1 or more and 6 or less carbon atoms |
| $R^3$ | Hydrogen atom | Hydrogen atom | Hydrogen atom | Hydrogen atom |
| $R^4$ | Hydrogen atom | Hydrogen atom | Hydrogen atom | Hydrogen atom |
| $R^5$ | Hydrogen atom | Hydrogen atom | Hydrogen atom | Hydrogen atom |
| $R^6$ | Hydrogen atom | Hydrogen atom | Hydrogen atom | Hydrogen atom |

The compound represented by formula (III) is more preferably, e.g., any of the following compounds.

[Chemical Formula 5]

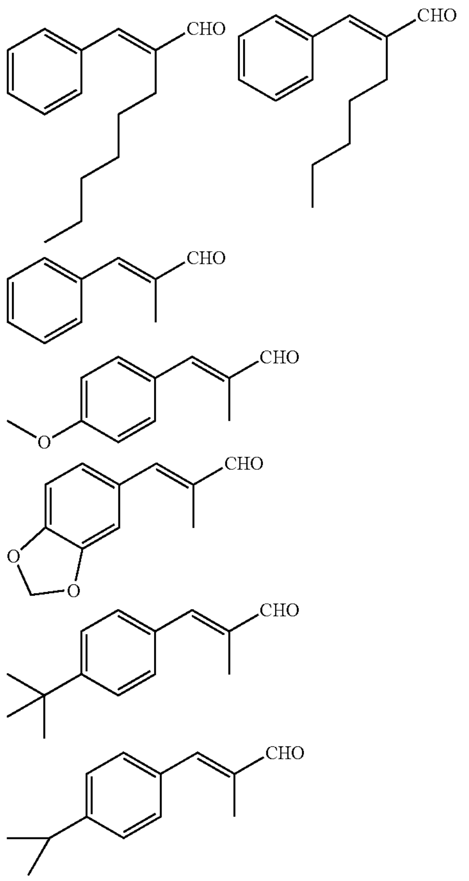

Titanium Oxide

The titanium oxide may be an anatase-type, a rutile-type, a brookite-type, or a mixture thereof. From the viewpoints of the yield and selectivity, the titanium oxide preferably contains an anatase-type, and more preferably the content of the anatase-type relative to the whole titanium oxide is 60% by mass or more, further preferably 80% by mass or more, and still further preferably 95% by mass or more, and preferably 100% by mass or less.

In the present invention, the titanium oxide is used in an amount of preferably 1% by mass or more, more preferably 2% by mass or more, and further preferably 5% by mass or more relative to the compound of formula (I) from the viewpoints of the yield and selectivity. Furthermore, the titanium oxide is used in an amount of preferably 50% by mass or less, more preferably 30% by mass or less, and further preferably 20% by mass or less relative to the compound of formula (I) from the viewpoint of the low-cost production. From these viewpoints, the titanium oxide is used in an amount of preferably 1% by mass or more and 50% by mass or less, more preferably 2% by mass or more and 30% by mass or less, and further preferably 5% by mass or more and 20% by mass or less relative to the compound of formula (I).

Specifically, the titanium oxide is used in an amount of preferably 1 part by mass or more, more preferably 2 parts by mass or more, and further preferably 5 parts by mass or more relative to 100 parts by mass of the compound of formula (I) from the viewpoints of the yield and selectivity. Furthermore, the titanium oxide is used in an amount of preferably 50 parts by mass or less, more preferably 30 parts by mass or less, and further preferably 20 parts by mass or less relative to 100 parts by mass of the compound of formula (I) from the viewpoint of the low-cost production. From these viewpoints, the titanium oxide is used in an amount of preferably 1 part by mass or more and 50 parts by mass or less, more preferably 2 parts by mass or more and 30 parts by mass or less, and further preferably 5 parts by mass or more and 20 parts by mass or less relative to 100 parts by mass of the compound of formula (I).

The primary particle diameter of the titanium oxide is, e.g., 1 nm or more and 50 nm or less, preferably 3 nm or more and 40 nm or less, and more preferably 5 nm or more and 30 nm or less. The primary particle diameter is measured by an X-ray diffraction method.

The BET specific surface area of the titanium oxide is determined by, e.g., a nitrogen adsorption method. The BET specific surface area of the titanium oxide is, e.g., 30 $m^2/g$ or more and 500 $m^2/g$ or less, preferably 40 $m^2/g$ or more and 400 $m^2/g$ or less, and more preferably 50 $m^2/g$ or more and 300 $m^2/g$ or less.

The crystallite diameter of the titanium oxide is 80 Å or more, more preferably 100 Å or more, and further preferably 120 Å or more from the viewpoints of the yield and selectivity. From the same viewpoints, the crystallite diameter thereof is preferably 500 Å or less, more preferably 400 Å or less, and further preferably 300 Å or less. Specifically, the crystallite diameter of the titanium oxide is preferably 80 Å or more and 500 Å or less, more preferably 100 Å or more and 400 Å or less, and further preferably 120 Å or more and 300 Å or less. The crystallite diameter can be measured by the method described in Examples. A catalogue value may be used in a case of using a commercially available titanium oxide.

The titanium oxide may be produced by a sulfuric acid method, a chlorine method, etc., and those produced by a sulfuric acid method are preferred.

The titanium oxide may be produced by a gas phase method, a liquid phase method, etc., and those produced by a liquid phase method are preferred.

Solvent

In the step of the present invention, when the solvent is used, the amount of the solvent relative to the compound of formula (I) and the compound of formula (II) is 50% by mass or less, preferably 30% by mass or less, more preferably 10% by mass or less, and further preferably 5% by mass or less, and preferably 0% by mass or more, and more preferably substantially 0% by mass from the viewpoints of the yield and selectivity. The term "substantially" used herein means that the solvent is intentionally not used, and does not exclude a case in which the solvent is contained unintentionally. From these viewpoints, the amount of the solvent relative to 100 parts by mass in total of the compound of formula (I) and the compound of formula (II) is preferably 0 parts by mass or more and 30 parts by mass or less, more preferably 0 parts by mass or more and 10 parts by mass or less, and further preferably 0 parts by mass or more and 5 parts by mass or less.

Examples of the solvent include alcohol solvents such as methanol, n-propanol and isopropanol, t-butanol, 1-butanol, 1-hexanol, and glycerin; ketone solvents such as acetone, methyl ethyl ketone (MEK), methyl isobutyl ketone (MIBK), cyclohexanone, methyl hexyl ketone, diisobutyl ketone, diacetone alcohol, and isophorone; ether solvents such as diethyl ether, tetrahydrofuran (THF), and dioxane; non-aromatic hydrocarbon solvents such as hexane, petroleum ether, liquid paraffin, squalane, and squalene; and unsubstituted or substituted aromatic hydrocarbon solvents having 6 to 12 carbon atoms such as benzene, toluene, and xylene. The solvent contains preferably a hydrocarbon solvent and more preferably an aromatic hydrocarbon solvent.

The amount of the aromatic hydrocarbon solvent relative to the compound of formula (I) and the compound of formula (II) is preferably 50% by mass or less, more preferably 30% by mass or less, further preferably 10% by mass or less, and still further preferably 5% by mass or less, and preferably 0% by mass or more, and more preferably substantially 0% by mass from the viewpoints of the yield and selectivity.

The solvent contains the aromatic hydrocarbon solvent in an amount of preferably 50% by mass or more and 100% by mass or less, more preferably 80% by mass or more and 100% by mass or less, and further preferably 95% by mass or more and 100% by mass or less.

Reaction Step

In the present invention, the step of reacting the compound of formula (I) with the compound of formula (II) to provide the α,β-unsaturated aldehyde of formula (III) may be performed, for example, by charging the titanium oxide as a catalyst, the compound of formula (I), and the compound of formula (II) into a reaction vessel, and stirring the reaction mixture. Alternatively, the step may be performed by charging the titanium oxide as a catalyst and the compound of formula (II) into a reaction vessel, and adding the compound of formula (I) dropwise.

In the present invention, the amount of the compound of formula (II) relative to the compound of formula (I) is preferably 0.8 molar equivalents or more, more preferably 1.0 molar equivalent or more, further preferably 1.2 molar equivalents or more, and still further preferably 1.5 molar equivalents or more from the viewpoints of the yield and selectivity. Furthermore, the amount thereof is preferably 15 molar equivalents or less, more preferably 10 molar equivalents or less, further preferably 7 molar equivalents or less, and still further preferably 5 molar equivalents or less from the viewpoint of the low-cost production. From these viewpoints, the amount of the compound of formula (II) relative to the compound of formula (I) is preferably 0.8 molar equivalents or more and 15 molar equivalents or less, more preferably 1.0 molar equivalent or more and 10 molar equivalents or less, further preferably 1.2 molar equivalents or more and 7 molar equivalents or less, and still further preferably 1.5 molar equivalents or more and 5 molar equivalents or less.

In the present invention, the step of reacting the compound of formula (I) with the compound of formula (II) to provide the α,β-unsaturated aldehyde of formula (III) is performed preferably at 20° C. or higher, more preferably at 25° C. or higher, and further preferably at 50° C. or higher, and preferably at 200° C. or lower, more preferably at 180° C. or lower, and further preferably at 160° C. or lower, and preferably at 20° C. or higher and 200° C. or lower, more preferably at 25° C. or higher and 180° C. or lower, and further preferably at 50° C. or higher and 160° C. or lower from the viewpoint of reaction efficiency.

In the present invention, the step of reacting the compound of formula (I) with the compound of formula (II) to provide the α,β-unsaturated aldehyde of formula (III) may be performed in an atmosphere of inert gas from the viewpoint of reaction efficiency. The inert gas is preferably nitrogen or noble gas (elements in Group 18), and more preferably nitrogen from the viewpoint of reaction efficiency. Examples of the noble gas include argon and helium, and argon is preferred.

The present invention encompasses the following aspects.

<1> A method for producing an α,β-unsaturated aldehyde, including a step of reacting a compound represented by formula (I) with a compound represented by formula (II) in the presence or absence of a solvent to provide a compound represented by formula (III), wherein titanium oxide is used as a catalyst in the step, and an amount of the solvent is 50 parts by mass or less relative to 100 parts by mass in total of the compound of formula (I) and the compound of formula (II).

[Chemical Formula 6]

(I)

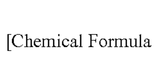

(II)

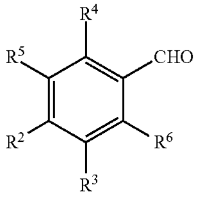

-continued (III)

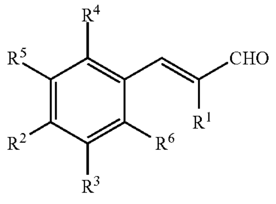

In the above formulae, $R^1$ represents a hydrogen atom or an alkyl group having 1 or more and 10 or less of carbon atoms, $R^2$ represents a hydrogen atom, an alkyl group having 1 or more and 6 or less of carbon atoms, or an alkoxy group having 1 or more and 6 or less of carbon atoms, and $R^3$ represents a hydrogen atom or an alkyl group having 1 or more and 3 or less of carbon atoms, or $R^2$ and $R^3$ form 1,3-dioxolane together with carbon atoms to which $R^2$ and $R^3$ are attached, and $R^4$, $R^5$, and $R^6$ each independently represent a hydrogen atom or an alkyl group having 1 or more and 3 or less of carbon atoms.

<2> The method according to <1>, wherein the amount of the solvent is 0 parts by mass or more and 30 parts by mass or less relative to 100 parts by mass in total of the compound of formula (I) and the compound of formula (II).

<3> The method according to <1> or <2>, wherein the amount of the solvent is 0 parts by mass or more and 1.0 parts by mass or less relative to 100 parts by mass in total of the compound of formula (I) and the compound of formula (II).

<4> The method according to any of <1> to <3>, wherein the amount of the solvent is 0 parts by mass or more and 5 parts by mass or less relative to 100 parts by mass in total of the compound of formula (I) and the compound of formula (II).

<5> The method according to any of <1> to <4>, wherein the amount of the solvent is substantially 0 parts by mass relative to 100 parts by mass in total of the compound of formula (I) and the compound of formula (II).

<6> The method according to any of <1> to <5>, wherein an amount of the compound represented by formula (II) is 0.8 molar equivalents or more and 15 molar equivalents or less relative to the compound represented by formula (I) in the step.

<7> The method according to any of <1> to <6>, wherein an amount of the compound represented by formula (II) is 1.0 molar equivalent or more and 10 molar equivalents or less relative to the compound represented by formula (I) in the step.

<8> The method according to any of <1> to <7>, wherein an amount of the compound represented by formula (II) is 1.2 molar equivalents or more and 7 molar equivalents or less relative to the compound represented by formula (I) in the step.

<9> The method according to any of <1> to <8>, wherein $R^1$ is an alkyl group having 3 to 8 carbon atoms.

<10> The method according to any of <1> to <9>, wherein $R^2$ represents a hydrogen atom or an alkyl group having 1 or more and 6 or less of carbon atoms, and $R^3$ represents a hydrogen atom or an alkyl group having 1 or more and 3 or less of carbon atoms.

<11> The method according to any of <1> to <10>, wherein the compound represented by formula (II) is a compound represented by any of the following formulae.

[Chemical Formula 7]

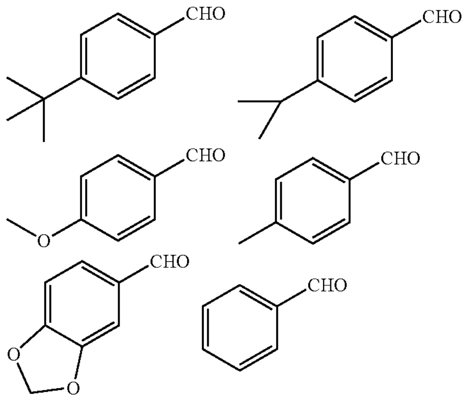

<12> The method according to any of <1> to <11>, wherein the titanium oxide contains an anatase-type titanium oxide.

<13> The method according to any of <1> to <12>, wherein the titanium oxide has a crystallite diameter of 80 Å or more and 500 Å or less.

<14> The method according to any of <1> to <13>, wherein the titanium oxide has a crystallite diameter of 100 Å or more and 500 Å or less.

<15> The method according to any of <1> to <14>, wherein the titanium oxide has a crystallite diameter of 100 Å or more and 400 Å or less.

<16> The method according to any of <1> to <15>, wherein the titanium oxide has a crystallite diameter of 120 Å or more and 300 Å or less.

<17> The method according to any of <1> to <16>, wherein the titanium oxide is used in an amount of 1 part by mass or more and 50 parts by mass or less relative to 100 parts by mass of the compound of formula (I).

<18> The method according to any of <1> to <17>, wherein the titanium oxide is used in an amount of 2 parts by mass or more and 30 parts by mass or less relative to 100 parts by mass of the compound of formula (I).

<19> The method according to any of <1> to <18>, wherein the titanium oxide is used in an amount of 5 parts by mass or more and 20 parts by mass or less relative to 100 parts by mass of the compound of formula (I).

<20> The method according to any of <1> to <19>, wherein the solvent contains a hydrocarbon solvent.

<21> The method according to any of <1> to <20>, wherein the solvent contains an aromatic hydrocarbon solvent.

<22> The method according to any of <1> to <21>, wherein the solvent contains the aromatic hydrocarbon solvent in an amount of 50% by mass or more and 100% by mass or less.

<23> The method according to any of <1> to <22>, wherein the solvent contains the aromatic hydrocarbon solvent in an amount of 80% by mass or more and 100% by mass or less.

<24> The method according to any of <1> to <23>, wherein the solvent contains the aromatic hydrocarbon solvent in an amount of 95% by mass or more and 100% by mass or less.

<25> The method according to any of <1> to <24>, wherein the step is performed at 20° C. or higher and 200° C. or lower.

<26> The method according to any of <1> to <25>, wherein the step is performed at 25° C. or higher and 180° C. or lower.

<27> The method according to any of <1> to <26>, wherein the step is performed at 50° C. or higher and 160° C. or lower.

<28> The method according to any of <1> to <27>, wherein the compound represented by formula (I) is octanal, the compound represented by formula (II) is benzaldehyde, and the compound represented by formula (III) is hexyl cinnamic aldehyde.

EXAMPLES

In the following examples and comparative examples, the term "%" means "% by mass" unless otherwise specified.

The materials used in the reaction were as follows:

benzaldehyde: manufactured by Wako Pure Chemical Industries, Ltd., Wako special grade;

octanal: manufactured by Kao Corporation;

toluene: manufactured by Wako Pure Chemical Industries, Ltd., Wako special grade;

tetradecane: manufactured by Wako Pure Chemical Industries, Ltd., Wako special grade; and diethyl ether: manufactured by Wako Pure Chemical Industries, Ltd., Wako special grade.

Example 1

Production of Hexyl Cinnamic Aldehyde (formula (III-1))

[Chemical Formula 8]

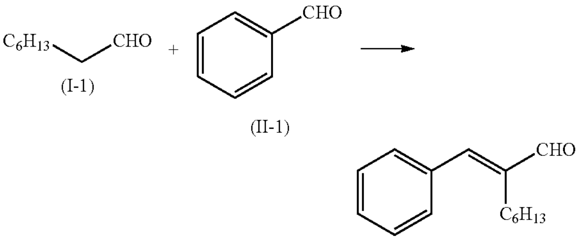

(I-1) (II-1) (III-1)

In a reaction tube 34 mm in inner diameter equipped with a condenser, the following were placed: titanium oxide as a catalyst (SSP-M, an anatase-type titanium oxide manufactured by SAKAI CHEMICAL INDUSTRY CO., LTD., in accordance with a sulfuric acid method (liquid phase method), 0.19 g, 10% by mass relative to octanal, 10 parts by weight relative to 100 parts by mass of the compound of formula (I)); octanal (formula (I-1), 1.9 g, 15.0 mmol); benzaldehyde (formula (II-1), 8.0 g, 75.0 mmol, 5 molar equivalents relative to octanal); and tetradecane (GC internal standard, 0.2 g). The inside of the reaction tube was replaced with nitrogen, and the liquid mixture in the reaction tube was stirred for 4 hours at 150° C. Then, the reaction tube was cooled to 30° C. to finish the reaction.

Using gas chromatography (GC), a quantitative analysis of the filtered reaction product was performed by an internal standard method to determine the composition for each component of the reaction product. The results of the reaction were calculated by the following formulae based on the composition of the reaction product thus obtained. The internal standard substance was tetradecane, and the solvent was diethyl ether. Table 2 below shows the calculated yield of hexyl cinnamic aldehyde (relative to octanal), selectivity of hexyl cinnamic aldehyde (relative to benzaldehyde), and HCA-to-dimer formation ratio.

Specifically, 0.2 mL of the reaction solution was sampled, put in a screw bottle, and precisely weighed. To dilute the reaction solution, 4 mL of diethyl ether was added thereto. The solution was filtered with a membrane filter (polytetrafluoroethylene (PTFE), 0.2 μm) to remove the catalyst, and the filtrate thus obtained was analyzed by GC.

The GC analysis used both DB-1 column (GC column, 100% dimethylpolysiloxane manufactured by Agilent Technologies Japan, Ltd.) and DB-WAX column (GC column, polyethylene glycol manufactured by Agilent Technologies Japan, Ltd.).

Yield of Hexyl Cinnamic Aldehyde (Relative to Octanal)

The yield of the target hexyl cinnamic aldehyde (relative to octanal) was calculated by the following formula. A larger value indicates better yield.

[Formula 1]

$$\text{Yield of hexyl cinnamic aldehyde (relative to octanal)[\%]} = \frac{\left[\dfrac{\text{[Mass of hexyl cinnamic aldehyde in product]}}{\text{[Molecular weight of hexyl cinnamic aldehyde]}}\right]}{\left[\dfrac{\text{[Mass of charged octanal]}}{\text{[Molecular weight of octanal]}}\right]} \times 100$$

Selectivity of Hexyl Cinnamic Aldehyde (Relative to Benzaldehyde)

The selectivity of the hexyl cinnamic aldehyde (relative to benzaldehyde), which is a measure of the disproportionation of aldehydes, was calculated by the following formula. A larger value indicates better selectivity.

[Formula 2]

$$\text{Selectivity of hexyl cinnamic aldehyde (relative to benzaldehyde)[\%]} = \frac{\left[\dfrac{\text{[Mass of hexyl cinnamic aldehyde in product]}}{\text{[Molecular weight of hexyl cinnamic aldehyde]}}\right]}{\left[\dfrac{\text{[Mass of charged benzaldehyde]} - \text{[Mass of benzaldehyde in product]}}{\text{[Molecular weight of benzaldehyde]}}\right]} \times 100$$

HCA-to-Dimer Formation Ratio

A formation ratio of dimers, which are products of the dimerization of aldehydes, to HCA, which is a target product, was calculated by the following formula.

A larger value indicates less by-products.

[Formula 3]

$$HCA\text{-to-dimer formation ratio [-]} = \frac{\left[\dfrac{\text{[Mass of hexyl cinnamic aldehyde in product]}}{\text{[Molecular weight of hexyl cinnamic aldehyde]}}\right]}{\left[\dfrac{\text{[Mass of dimer in product]}}{\text{[Molecular weight of dimer]}}\right]}$$

Example 2

Example 2 was performed in the same manner as Example 1 except for the use of titanium oxide (AMT-600, an anatase-type titanium oxide manufactured by TAYCA CORPORATION in accordance with a sulfuric acid method (liquid phase method)) in place of titanium oxide (SSP-M manufactured by SAKAI CHEMICAL INDUSTRY CO., LTD.) as a catalyst. Table 2 shows the evaluation results of the product thus obtained.

Example 3

Example 3 was performed in the same manner as Example 1 except for the use of titanium oxide (MC-150, an anatase-type titanium oxide manufactured by ISHIHARA SANGYO KAISHA, LTD., in accordance with a sulfuric acid method (liquid phase method)) in place of titanium oxide (SSP-M manufactured by SAKAI CHEMICAL INDUSTRY CO., LTD.) as a catalyst. Table 2 shows the evaluation results of the product thus obtained.

Example 4

Example 4 was performed in the same manner as Example 1 except for the use of titanium oxide (MC-50, an anatase-type titanium oxide manufactured by ISHIHARA SANGYO KAISHA, LTD., in accordance with a sulfuric acid method (liquid phase method)) in place of titanium oxide (SSP-M manufactured by SAKAI CHEMICAL INDUSTRY CO., LTD.) as a catalyst. Table 2 shows the evaluation results of the product thus obtained.

Example 5

Example 5 was performed in the same manner as Example 1 except for the use of titanium oxide (MC-90L, an anatase-type titanium oxide manufactured by ISHIHARA SANGYO KAISHA, LTD., in accordance with a sulfuric acid method (liquid phase method)) in place of titanium oxide (SSP-M manufactured by SAKAI CHEMICAL INDUSTRY CO., LTD.) as a catalyst. Table 2 shows the evaluation results of the product thus obtained.

Example 6

Example 6 was performed in the same manner as Example 1 except that the amount of benzaldehyde relative to octanal was changed to 1.5 molar equivalents instead of 5 molar equivalents. Table 2 shows the evaluation results of the product thus obtained.

Example 7

Example 7 was performed in the same manner as Example 1 except that toluene as a solvent (3.0 g, 30% by mass relative to the total amount of the compound of formula (I) and the compound of formula (ID) was placed in the reaction tube together with the catalyst, octanal, benzaldehyde, etc. Table 2 shows the evaluation results of the product thus obtained.

Example 8

In a 200 mL separable flask, the following were placed: titanium oxide as a catalyst (MC-90L, an anatase-type titanium oxide manufactured by ISHIHARA SANGYO KAISHA, LTD., in accordance with a sulfuric acid method (liquid phase method), 19.2 g, 30% by mass relative to octanal, 30 parts by weight relative to 100 parts by mass of the compound of formula (I)); and benzaldehyde (formula (II-1), 80.0 g, 0.75 mol, 1.5 molar equivalents relative to octanal). A mechanical stirrer, a thermometer, a Dean-Stark trap, a condenser, a nitrogen line, and an aldehyde supply line were attached to the separable flask. An octanal supply line was connected with a dropping pump to supply octanal at a constant speed. The inside of the reaction tube was replaced with nitrogen and then heated to 150° C., and the mixture in the separable flask was stirred. When the temperature reached 150° C., octanal (formula (I-1)) was supplied to the reaction mixture in the separable flask using the dropping pump. A total of 64 g (0.5 mol) of octanal was supplied to the reaction mixture in 6 hours, at a supply rate of 12.8 g/h in the former 3 hours and at a supply rate of 8.5 g/h in the latter 3 hours. Thereafter, the reaction mixture was continuously stirred at 150° C. for 0.5 hours. The separable flask was then cooled to 30° C. to finish the reaction. Table 2 shows the evaluation results of the product thus obtained.

Example 9

Example 9 was performed in the same manner as Example 1 except for the use of titanium oxide (TK-1460, an anatase-type titanium oxide manufactured by TAYCA CORPORATION in accordance with a sulfuric acid method (liquid phase method)) in place of titanium oxide (SSP-M manufactured by SAKAI CHEMICAL INDUSTRY CO., LTD.) as a catalyst. Table 2 shows the evaluation results of the product thus obtained.

Comparative Example 1

Comparative Example 1 was performed in the same manner as Example 1 except for the use of magnesium oxide (Kyowamag 30 manufactured by Kyowa Chemical Industry Co., Ltd., 0.19 g, 10% by mass relative to octanal) in place of titanium oxide (SSP-M manufactured by SAKAI CHEMICAL INDUSTRY CO., LTD., 0.19 g, 10% by mass relative to octanal) as a catalyst. Table 3 shows the evaluation results of the product thus obtained.

Comparative Example 2

Comparative Example 2 was performed in the same manner as Example 1 except for the use of hydrotalcite (hydrotalcite manufactured by Kyowa Chemical Industry Co., Ltd., 0.19 g, 10% by mass relative to octanal) in place of titanium oxide (SSP-M manufactured by SAKAI CHEMICAL INDUSTRY CO., LTD., 0.19 g, 10% by mass relative to octanal) as a catalyst. Table 3 shows the evaluation results of the product thus obtained.

Comparative Example 3

Comparative Example 3 was performed in the same manner as Example 1 except for the use of aluminophosphate (aluminophosphate manufactured by KANTO CHEMICAL CO., INC., 0.19 g, 10% by mass relative to octanal) in place of titanium oxide (SSP-M manufactured by SAKAI CHEMICAL INDUSTRY CO., LTD., 0.19 g, 10% by mass relative to octanal) as a catalyst. Table 3 shows the evaluation results of the product thus obtained.

Comparative Example 4

Comparative Example 4 was performed in the same manner as Example 1 except for the use of silicoaluminophosphate zeolite (SAPO-34 manufactured by JGC Catalysts and Chemicals Ltd., 0.19 g, 10% by mass relative to octanal) in place of titanium oxide (SSP-M manufactured by SAKAI CHEMICAL INDUSTRY CO., LTD., 0.19 g, 10% by mass relative to octanal) as a catalyst. Table 3 shows the evaluation results of the product thus obtained.

Comparative Example 5

Comparative Example 5 was performed in the same manner as Example 1 except that toluene as a solvent (7.4 g, 75% by mass relative to the total amount of the compound of formula (I) and the compound of formula (II)) was placed in the reaction tube together with the catalyst, octanal, benzaldehyde, etc. Table 3 shows the evaluation results of the product thus obtained.

Tables 2 and 3 below summarize the reaction conditions and results in Examples 1 to 9 and Comparative Examples 1 to 5. Table 2 also shows the primary particle diameter of the titanium oxide used as a catalyst, the sulfur content, the BET specific surface area, and the crystallite diameter.

Primary Particle Diameter

Using an X-ray diffraction instrument (model "MiniFlex600" manufactured by Rigaku Corporation), the primary particle diameter was determined by an X-ray diffraction method from a peak of 2θ=25° to 26°.

BET Specific Surface Area

Using a specific surface area measuring instrument (model "FlowSorbIII" manufactured by Micromeritics Instrument Corporation), the BET specific surface area was measured.

Method for Measuring the Crystallite Diameter of Titanium Oxide in Powder X-Ray Diffraction Measurement Using a powder X-ray diffraction instrument (model "MiniFlex600" manufactured by Rigaku Corporation), a half-width of a peak at 2θ of 25° to 26° is measured by a powder X-ray diffraction measurement to determine the crystallite diameter of titanium oxide by the Scherrer equation represented by the following general formula (S) (where K=0.9, λ=1.5418 [Å]).

[Formula 4]

$$D=\lambda K/(\beta\cos\theta) \quad (S)$$

In general formula (S),

D represents a crystallite diameter [Å],

λ represents a wavelength of X-ray [ÅA],

K represents a Scherrer constant, and

β represents a half-width of a peak at 2θ of 25° to 26°.

The unit of β and θ is radian.

TABLE 2

| | | Example 1 | Example 2 | Example 3 | Example 4 | Example 5 | Example 6 | Example 7 | Example 8 | Example 9 |
|---|---|---|---|---|---|---|---|---|---|---|
| Catalyst | Catalyst | Titanium oxide | Titanium oxide | Titanium oxide | Titanium oxide | Titanium oxide | Titanium oxide | Titanium oxide | Titanium oxide | Titanium oxide |
| | Maker | SAKAI CHEMICAL INDUSTRY CO., LTD. | TAYCA COR-POR-ATION | ISHIHARA SANGYO KAISHA, LTD. | ISHIHARA SANGYO KAISHA, LTD. | ISHIHARA SANGYO KAISHA, LTD. | SAKAI CHEMICAL INDUSTRY CO., LTD. | SAKAI CHEMICAL INDUSTRY CO., LTD. | ISHIHARA SANGYO KAISHA, LTD. | TAYCA CORPOR-ATION |
| | Product name | SSP-M | AMT-600 | MC-150 | MC-50 | MC-90L | SSP-M | SSP-M | MC-90L | TK-1460 |
| | Primary particle diameter (nm) | 13 | 28 | 6 | 25 | 19 | 13 | 13 | 19 | 22 |
| | Cry-stallite diameter (Å) | 162 | 207 | 124 | 187 | 184 | 162 | 162 | 184 | 98 |
| | BET specific surface area ($m^2/g$) | 103 | 55 | 273 | 54 | 90 | 103 | 103 | 90 | 108 |
| Ben-zaldehyde equivalent | [Molar equiv-alent] | 5 | 5 | 5 | 5 | 5 | 1.5 | 5 | 1.5 | 5 |
| Octanal supply method | | Added at a time in initial stage | Added at a time in initial stage | Added at a time in initial stage | Added at a time in initial stage | Added at a time in initial stage | Added at a time in initial stage | Added at a time in initial stage | Dropping | Added at a time in initial stage |
| Solvent | Solvent | None | None | None | None | None | None | Toluene | None | None |
| | Amount of solvent [% by mass] | — | — | — | — | — | — | 30 | — | — |
| Reaction time | [hours] | 4 | 4 | 4 | 4 | 4 | 4 | 4 | 4 | 4 |
| Yield of hexyl cinnamic aldehyde (relative to octanal) | [%] | 87.0 | 87.3 | 86.5 | 80.1 | 87.0 | 66.0 | 74.3 | 90.8 | 60.4 |
| Selectivity of hexyl cinnamic aldehyde (relative to ben-zaldehyde) | [%] | 92.7 | 92.3 | 90.4 | 95.6 | 94.2 | 77.6 | 93.3 | 90.8 | 87.0 |
| HCA-to-dimer formation ratio | [–] | 15.7 | 15.3 | 14.7 | 11.4 | 14.7 | 5.5 | 11.1 | 37.9 | 8.7 |

TABLE 3

| | | Comparative Example 1 | Comparative Example 2 | Comparative Example 3 | Comparative Example 4 | Comparative Example 5 |
|---|---|---|---|---|---|---|
| Catalyst | Catalyst | Magnesium oxide | Hydrotalcite | Aluminophosphate | Silicoalumino-phosphate zeolite | Titanium oxide |
| | Maker | Kyowa Chemical Industry Co., Ltd. | Kyowa Chemical Industry Co., Ltd. | KANTO CHEMICAL CO., INC. | JGC Catalysts and Chemicals Ltd. | SAKAI CHEMICAL INDUSTRY CO., LTD. |
| | Product name | Kyowamag 30 | Hydrotalcite | Aluminophosphate | SAPO-34 | SSP-M |
| Benzaldehyde equivalent | [Molar equivalent] | 5 | 5 | 5 | 5 | 5 |
| Octanal supply method | | Added at a time in initial stage | Added at a time in initial stage | Added at a time in initial stage | Added at a time in initial stage | Added at a time in initial stage |
| Solvent | Solvent | None | None | None | None | Toluene |
| | [% by mass] | — | — | — | — | 75 |
| Reaction time | [hours] | 4 | 4 | 4 | 4 | 4 |
| Yield of hexyl cinnamic aldehyde (relative to octanal) | [%] | 49.2 | 55.4 | 49.2 | 47.4 | 24.3 |

TABLE 3-continued

| | | Comparative Example 1 | Comparative Example 2 | Comparative Example 3 | Comparative Example 4 | Comparative Example 5 |
|---|---|---|---|---|---|---|
| Selectivity of hexyl cinnamic aldehyde (relative to benzaldehyde) | [%] | 78.8 | 85.5 | 78.8 | 82.1 | 69.3 |
| HCA-to-dimer formation ratio | | 2.9 | 3.0 | 2.9 | 4.5 | 5.4 |

Tables 2 and 3 confirmed that the use of titanium oxide as a catalyst in the step of reacting the compound of formula (I) with the compound of formula (II) to provide the α,β-unsaturated aldehyde of formula (III) improves the selectivity of the α,β-unsaturated aldehyde (relative to the compound of formula (II)) and the yield of the α,β-unsaturated aldehyde (relative to the compound of formula (I)) while reducing the formation of by-products.

The production method of the present invention enables production of a target aldehyde at a high yield with satisfactory selectivity while reducing the formation of by-products, thereby producing an α,β-unsaturated aldehyde with high efficiency and high purity. Such a production method can be used suitably as a production method of an aldehyde that is useful as a fragrance material.

The invention claimed is:

1. A method for producing an α,β-unsaturated aldehyde, comprising reacting a compound represented by formula (I) with a compound represented by formula (II) in the presence or absence of a solvent to provide a compound represented by formula (III), wherein said reacting is conducted in the presence of a titanium oxide catalyst, an amount of the solvent is 50 parts by mass or less relative to 100 parts by mass in total of the compound of formula (I) and the compound of formula (II),

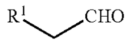

(I)

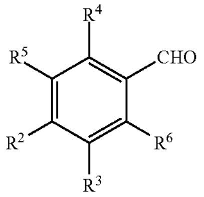

(II)

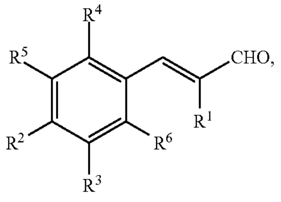

(III)

and the titanium oxide has a crystallite diameter of 100 Å or more and 400 Å or less, where $R^1$ represents a hydrogen atom or an alkyl group having 1 or more and 10 or less carbon atoms, $R^2$ represents a hydrogen atom, an alkyl group having 1 or more and 6 or less carbon atoms, or an alkoxy group having 1 or more and 6 or less carbon atoms, and $R^3$ represents a hydrogen atom or an alkyl group having 1 or more and 3 or less carbon atoms, or $R^2$ and $R^3$ form 1,3-dioxolane together with carbon atoms to which $R^2$ and $R^3$ are attached, and $R^4$, $R^5$, and $R^6$ each independently represent a hydrogen atom or an alkyl group having 1 or more and 3 or less carbon atoms.

2. The method according to claim 1, wherein the amount of the solvent is 0 parts by mass or more and 30 parts by mass or less relative to 100 parts by mass in total of the compound of formula (I) and the compound of formula (II).

3. The method according to claim 1, wherein the amount of the solvent is 0 parts by mass or more and 10 parts by mass or less relative to 100 parts by mass in total of the compound of formula (I) and the compound of formula (II).

4. The method according to claim 1, wherein an amount of the compound represented by formula (II) is 0.8 molar equivalents or more and 15 molar equivalents or less relative to the compound represented by formula (I).

5. The method according to claim 1, wherein $R^1$ is an alkyl group having 3 or more and 8 or less carbon atoms.

6. The method according to claim 1, wherein $R^2$ represents a hydrogen atom or an alkyl group having 1 or more and 6 or less carbon atoms, and $R^3$ represents a hydrogen atom or an alkyl group having 1 or more and 3 or less carbon atoms.

7. The method according to claim 1, wherein the compound represented by formula (II) is a compound represented by any of the following formulae

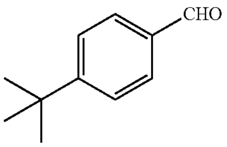

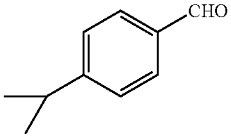

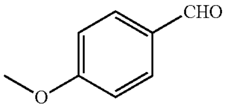

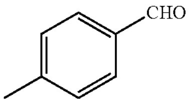

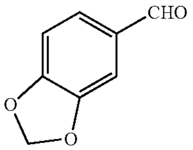

-continued

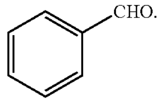

8. The method according to claim 1, wherein the titanium oxide comprises an anatase-type titanium oxide.

9. The method according to claim 1, wherein the titanium oxide is present in an amount of 1 part by mass or more and 50 parts by mass or less relative to 100 parts by mass of the compound of formula (I).

10. The method according to claim 1, wherein the titanium oxide is present in an amount of 2 parts by mass or more and 30 parts by mass or less relative to 100 parts by mass of the compound of formula (I).

11. The method according to claim 1, wherein the reacting is performed at 20° C. or higher and 200° C. or lower.

12. The method according to claim 1, wherein the compound represented by formula (I) is octanal, the compound represented by formula (II) is benzaldehyde, and the compound represented by formula (III) is hexyl cinnamic aldehyde.

13. The method according to claim 1, wherein an amount of the compound represented by formula (II) is 1.2 molar equivalents or more and 7 molar equivalents or less relative to the compound represented by formula (I).

14. The method according to claim 1, wherein $R^2$ represents a hydrogen atom or an alkyl group having 1 or more and 6 or less of carbon atoms, and $R^3$ represents a hydrogen atom or an alkyl group having 1 or more and 3 or less of carbon atoms.

15. The method according to claim 1, wherein the titanium oxide has a crystallite diameter of 120 Å or more and 300 Å or less.

16. The method according to claim 1, wherein the solvent contains a hydrocarbon solvent.

17. The method according to claim 1, wherein the solvent contains an aromatic hydrocarbon solvent.

18. The method according to claim 1, wherein the reacting is performed at 50° C. or higher and 160° C. or lower.

* * * * *